US007747048B2

(12) United States Patent
Morns et al.

(10) Patent No.: US 7,747,048 B2
(45) Date of Patent: Jun. 29, 2010

(54) METHOD OF ANALYSING SEPARATION PATTERNS

(75) Inventors: Ian Morns, Tyne & Wear (GB); Anna Kapferer, Newcastle upon Tyne (GB); David Bramwell, Newcastle Upon Tyne (GB)

(73) Assignee: BioSignatures Limited (GB)

( * ) Notice: Subject to any disclaimer, the term of this patent is extended or adjusted under 35 U.S.C. 154(b) by 1239 days.

(21) Appl. No.: 11/212,477

(22) Filed: Aug. 26, 2005

(65) Prior Publication Data

US 2007/0014449 A1    Jan. 18, 2007

(30) Foreign Application Priority Data

Jul. 15, 2005    (GB) ................... 0514555.2

(51) Int. Cl.
G06K 9/00 (2006.01)
G01N 33/48 (2006.01)
G01N 33/50 (2006.01)

(52) U.S. Cl. ........................... 382/128; 702/19
(58) Field of Classification Search ................ 382/128, 382/129, 130–134; 702/19–21
See application file for complete search history.

(56) References Cited

U.S. PATENT DOCUMENTS

| | | | | |
|---|---|---|---|---|
| 4,969,204 | A | 11/1990 | Jones et al. | 382/240 |
| 5,073,963 | A | 12/1991 | Sammons et al. | 382/128 |
| 6,219,462 | B1 | 4/2001 | Anandan et al. | 382/294 |
| 6,404,905 | B1 * | 6/2002 | Taylor, Jr. | 382/128 |
| 6,480,618 | B1 | 11/2002 | Parekh et al. | |
| 6,513,025 | B1 | 1/2003 | Rosen | 706/45 |
| 6,675,104 | B2 | 1/2004 | Paulse et al. | 702/22 |
| 7,107,254 | B1 * | 9/2006 | Dumais et al. | 706/50 |
| 7,333,895 | B2 | 2/2008 | Hitt et al. | |
| 2004/0002118 | A1 | 1/2004 | Smilansky | 435/7.1 |
| 2004/0002930 | A1 | 1/2004 | Oliver et al. | 706/46 |

(Continued)

FOREIGN PATENT DOCUMENTS

EP    1298505    4/2003

(Continued)

OTHER PUBLICATIONS

Weinert et al., "Neural Networks for Protein Classification", 2004, Applied Bioinformatics, v. 3, n. 1, pp. 41-48.*

(Continued)

Primary Examiner—Aaron W Carter
(74) Attorney, Agent, or Firm—Clise, Billion & Cyr, P.A.; Tim Clise (57) ABSTRACT

The present invention relates principally to the statistical analysis of protein separation patterns. Specifically, the invention provides a method of performing operations on protein samples for the analysis of separation patterns, the method including separating a plurality of protein samples to produce a plurality of respective separation patterns; forming a representation of each separation pattern; building an importance map by iteratively recording performance values of classification models against locations in the importance map which correspond to locations in representations of separation patterns of data points used to build the classification models; and processing the importance map to identify important areas. Parts of the map which include high performance values indicate regions of the separation pattern which are statistically important in predicting a classification of the pattern.

46 Claims, 7 Drawing Sheets

U.S. PATENT DOCUMENTS

| | | | |
|---|---|---|---|
| 2004/0019574 A1 | 1/2004 | Meng et al. | |
| 2004/0024532 A1 | 2/2004 | Kincaid | 702/19 |
| 2004/0038417 A1* | 2/2004 | Cahill et al. | 436/86 |
| 2004/0098208 A1 | 5/2004 | Reeve et al. | 702/32 |
| 2004/0193378 A1 | 9/2004 | Gut et al. | 702/20 |
| 2005/0018887 A1 | 1/2005 | Breen | 382/128 |
| 2005/0032113 A1 | 2/2005 | Tanaka et al. | |
| 2005/0075875 A1 | 4/2005 | Shozakai et al. | |
| 2005/0100967 A1 | 5/2005 | Leslie et al. | 435/7.1 |
| 2005/0129302 A1 | 6/2005 | Smilansky et al. | 382/149 |
| 2005/0129303 A1 | 6/2005 | Smilansky et al. | 382/149 |
| 2007/0014450 A1* | 1/2007 | Morns et al. | 382/128 |
| 2007/0016606 A1* | 1/2007 | Morns et al. | 707/102 |
| 2007/0276610 A1* | 11/2007 | Korenberg | 702/19 |
| 2009/0055100 A1* | 2/2009 | Cahill et al. | 702/19 |

FOREIGN PATENT DOCUMENTS

| | | |
|---|---|---|
| EP | 1238366 | 4/2004 |
| GB | 2413695 | 11/2005 |
| GB | 2413696 | 11/2006 |
| WO | WO0145046 | 6/2001 |
| WO | WO03076896 | 9/2003 |
| WO | WO2004050825 | 6/2004 |
| WO | WO2005103706 | 11/2005 |

OTHER PUBLICATIONS

Rosengren, et al.; "Comparison of PDQuest and Progenesis software packages in the analysis of two-dimensional electrophoresis gels," Proteomics, vol. 3, No. 10, Oct. 2003 pp. 1936-1946.

M.R. Wilkins, et al (eds.), "Proteome Research: New Frontiers in Functional Genomics", Springer-Verlag, Berlin Heidelberg 1997, (132 pages, representing entire book).

International Search Report from PCT/GB2006/002548 dated Nov. 1, 2006, (5 pages).

International Search Report from PCT/GB2006/002581 dated Oct. 31, 2006, (4 pages).

International Search Report from PCT/GB2006/002585 dated Oct. 13, 2006, (5 pages).

* cited by examiner

METHOD OF ANALYSING SEPARATION PATTERNS

CROSS-REFERENCES TO RELATED APPLICATIONS

This application claims the benefit of United Kingdom Application Serial Number 0514555.2, filed Jul. 15, 2005, which application is incorporated herein by reference.

This application is related to, titled: A METHOD OF ANALYSING A REPRESENTATION OF A SEPARATION PATTERN, U.S. application Ser. No. 11/212,478, titled: A METHOD OF ANALYSING REPRESENTATIONS OF A SEPERATION PATTERNS, U.S. application Ser. No. 11/212,479, both of which are filed on even date herewith and incorporated by reference.

FIELD OF THE INVENTION

The present invention relates principally to the statistical analysis of protein separation patterns, and in particular to a method of identifying the parts of a separation pattern which are important in predicting a classification of the pattern.

BACKGROUND OF THE INVENTION

A proteome is a collection of proteins expressed by a genome at a particular moment. Proteomics is the study of proteomes in order to ascertain the differences between two different states of an organism, for example that of a healthy person and that of a person with cancer.

A preferred technique for separating proteins within a sample is two-dimensional gel electrophoresis. In this technique, proteins held within a porous gel are separated in a first direction using isoelectric focusing, before being separated in a second direction using a technique known as SDS-PAGE.

Isoelectric focusing is a technique in which proteins are electrophoresed in a polyacrylamide gel in which a pH gradient is established. Each protein migrates to a point in the gradient that corresponds to its isoelectric point (pI), the pH at which the protein has no net charge.

SDS-PAGE is a technique in which proteins are solubilised using the detergent sodium dodecyl sulphate (SDS), before being electrophoresed through a slab of polyacrylamide gel. Proteins migrate through the gel at a rate which is proportional to their molecular weight (MW).

The result of performing two-dimensional gel electrophoresis on a sample is a two-dimensional separation pattern.

Figure 1:
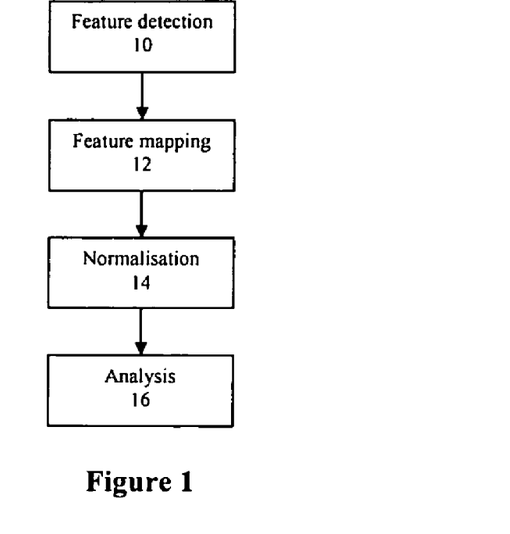
FIG. 1 is a flowchart representing a conventional method of analysing separation patterns.

A conventional method for analysing separation patterns as represented in FIG. 1 includes the following steps:—

Feature Detection 10

Detection of spots in a separation pattern. This step may involve correction for noise and background offsets. Often, different numbers of spots are detected in different patterns, resulting in missing spots.

Feature Mapping 12

Correspondences between spots in different patterns are identified, and indicated using a match vector joining the centres of detected spots in overlaid patterns. A warp is performed on the overlaid patterns to counteract geometric distortions of the gel.

Normalisation 14

The sum of all of the pixel intensities within a spot outline is the spot volume. This value is processed to produce a normalised volume which can be used to compare spot volumes between patterns.

Analysis 16

Certain criteria, for example the difference in size between corresponding spots in different patterns, are used to produce a list of interesting spots.

This conventional method has numerous disadvantages:—
1. Missing spots cause problems for statistical analysis of data.
2. Feature-based analysis introduces noise. Small differences in spot outline, background estimates, mapping etc can influence measured values.
3. The analysis step focuses on variance to differentiate groups. Subtle differences which may be used to differentiate classes may be overlooked because of high variance in other areas, which areas may not be useful in differentiating classes, and may be the result of noise.
4. Proteomics research usually involves supervised studies while many analysis techniques are unsupervised.
5. Basing the analysis on an increased number of samples exacerbates the problems of missing spots.
6. A large amount of information within the gels is discarded. The surrounding areas where no spots have been detected contain valuable information on background, noise and scaling that could be affecting the value of a measured spot.

A large proportion of supervised learning techniques suffer from having large numbers of variables in comparison to the number of class examples. With such a high ratio, it is often possible to build a classification model that has perfect discrimination performance, but the properties of the model may be undesirable in that it lacks generality, and that it is far too complex (given the task) and very difficult to examine for important factors.

Accordingly, it is desirable to provide a statistically sound framework for the analysis of bioparticle and biomolecular separation data.

It is further desirable to overcome some or all of the above-described problems.

SUMMARY OF THE INVENTION

According to a first aspect of the invention, there is provided a method of performing operations on protein samples for the analysis of separation patterns, the method including
separating a plurality of protein samples to produce a plurality of respective separation patterns;
forming a representation of each separation pattern;
building an importance map by iteratively recording performance values of classification models against locations in the importance map which correspond to locations in representations of separation patterns of data points used to build the classification models; and
processing the importance map to identify important areas.

According to a second aspect of the invention, there is provided a method of performing operations on protein samples for the analysis of separation patterns, the method comprising building an importance map by iteratively recording performance values of classification models against locations in the importance map which correspond to locations in representations of separation patterns of data points used to build the classification models; and processing the importance map to identify important areas.

By "representation" is meant any image, vector, table, database, or other collection of data representing a separation pattern. The data may have any dimensionality. By "separation pattern" is meant the result of any separation technique, including, but not limited to, gel electrophoresis, mass spectrometry, liquid chromatography, affinity binding, and capillary electrophoresis.

By "data point" is meant any constituent unit of data in the representation.

For example, in one embodiment, the representation is a two-dimensional image of a separation pattern obtained by gel electrophoresis, each pixel of the image constituting a data point.

The importance map has the same dimensionality as the representations used to build it. For example, for MS one dimensional vectors of results the importance map is in the form of a one dimensional vector of results, while for 2D images the importance map is two dimensional.

Parts of the importance map which include high performance values indicate regions of the separation pattern which are statistically important in predicting a classification of the pattern. The invention does not rely on the mistaken assumption that parts having a high variance are indicative of class.

By iteratively building models and recording the performance of each model against the location of each data point used in its construction, the invention provides a technique-independent, stochastic procedure. The importance map is robust to outliers (caused by, for example, data collection or process errors, or a particle of dust causing a spike on one of the gels) and noise, and allows the direct association of important factors with locations of data points in the representation, and thereby with parts of the separation patterns themselves.

As the procedure is iterative, a distribution of performances is generated for each location. This distribution gives a metric of the classification performance that can be expected whenever a data point at that particular location is included in a model.

As the number of iterations increases, the data points that are most predictive of classification converge towards higher values, and data points that are not predictive tend towards lower values.

Unlike the prior art, the invention provides the classification algorithms with all of the information in the representation (instead of discarding background information in gels).

The method may include the step of a building classification model based on a subset of the data points in the representations.

Building a classification model using whole representations, while possible, may result in perfect performance being obtained owing to a large number of variables compared to the number of classes. It is important that some models are not perfect, so that it may become apparent which areas of a representation are important. Building a classification model based on a subset of the data region reduces the number of variables used in the classification procedure, resulting in reduced performance.

In the case of the subset containing very few or no data points that are predictive of class, near chance performance is obtained. In the case of the subset containing data points that are highly predictive, the discrimination results are improved.

More particularly, the method may include iteratively performing the steps of
(1) building a subset including data points taken from a number of representations;
(2) partitioning the subset into a training set and a test set;
(3) building a classification model based on the training set;
(4) assessing the performance of the classification model on the test set to obtain a performance value; and
(5) recording the performance value against locations in the importance map which correspond to the locations in the representations of the data points.

Preferably, steps (1) to (5) are iteratively performed until the performance value at every location converges to within a predetermined tolerance.

Step (1) may include the steps of
(1a) selecting particular locations in a reference representation; and
(1b) building the subset by combining data points taken from each representation at the selected locations.

In this way, the same number of data points is taken from each representation, facilitating the processing of the data.

In step (1a), the locations may be selected randomly. Alternatively, a list of data points within a representation may be made and randomly shuffled.

The classification model may be built in step (3) using any one or more of the following techniques: discriminant analysis; flexible discriminant analysis; artificial neural networks; regression trees; genetic algorithms; support vector machines.

However, it is to be understood that the invention is not limited to any of these techniques.

The method may include, before step (1), the steps of normalising the representations, and/or registering the representations, and/or data reduction (to reduce the dimensionality of the data region).

Data reduction may include any one or more of the following techniques: partial least squares; independent component analysis; principal component analysis.

Attempting to produce a model based on unreduced data has the problem that the large number of data points and the corresponding number of dimensions makes computation difficult; and that, as the number of data points is large compared to the number of classifications, there is often a model with perfect performance.

Perfect performance is undesirable as the model can lack generality. A perfect model is likely to be too complex (given the task) and to be difficult to examine for important factors, and is unlikely to be relying on factors that relate to the experiment data of interest.

The performance value may be recorded as an average performance value or as a distribution of performance values. The distribution may be in the form of a confusion matrix (i.e. the prediction performance on a class by class basis).

Each representation may include a neighbourhood representing a region of a separation pattern, the neighbourhood including a plurality of data points. The method may comprise augmenting data by representing an entire region using each data point of the neighbourhood; and building a classification model using some or all of the data points.

This exploits the fact that data points in a representation of a separation pattern are usually highly locally correlated, i.e. there is usually far more resolution in the representation than in the signal which is represented.

By taking each data point of the neighbourhood as being representative of the entire region covered by that neighbourhood, the resolution of the representation is effectively reduced, while the number of measurements of that region is effectively increased.

Reducing the resolution of the representation reduces the number of variables used in the building of a classification model. Thus, the model is more likely to offer less than perfect performance, allowing a range of model performances to be obtained and facilitating the identification of parts of the separation pattern which are important in predicting its classification.

Unlike other data reduction processes, for example simple averaging, the invention does not discard data: each data point of a neighbourhood is taken as being an independent measurement of the region of the separation pattern covered by that neighbourhood, effectively increasing the number of separation patterns used in the model building process.

In addition, sensor-added noise is usually of a relatively high frequency, affecting few successive data points in the representation. The invention mitigates the impact of such noise as several measurements of the region covered by a neighbourhood are taken.

Thus, in effect, the invention trades resolution for class examples. This has several advantages:

- an improvement in supervised learning ability
- an improvement in the generality of the classification model
- reduced dimensionality
- improved tolerance to noise.

In one embodiment, the data augmentation step includes separating the data points of the neighbourhood into respective recombined representations, the location of a data point in a recombined representation corresponding to the location of its neighbourhood in the representation. In this way, an original representation may be transformed into a number of recombined representations each having a lower resolution. When a classification model is built, the recombined representations may be treated as though each represents a different separation pattern.

The method may include associating each recombined representation with a particular location of a data point in a neighbourhood. Maintaining this association constant throughout the procedure provides for computational efficiency. Alternatively, the association of recombined representations with locations may be varied between neighbourhoods. This is computationally more difficult, but can reveal any effect of a particular association.

The method may include varying the position of a particular neighbourhood in relation to the representation. This reveals whether the chosen position of that neighbourhood results in artifacts being obtained.

The method may include comparing a first distribution built using neighbourhoods of a first size to a second distribution built using neighbourhoods of a second size and selecting criteria based on the first and second sizes if a statistical change in the distributions is detected.

F-ratio or student t tests may be used to determined a probability threshold based on the probability that the distributions significantly differ in means. Alternatively, non-parametric tests may be used.

The method may include building a distribution in respect of each data point, the distribution including values of neighbouring data points.

This results in a distribution of likely values for each data point in the representation. The distributions of the neighbours of each data point can be used to predict how likely the value of that data point is, given what the case is in the rest of the representation. If all of the neighbours indicate that the value of the data point is unlikely, that data point probably represents a noise feature. This approach only works if the neighbours are good predictors of each other. As the size of the neighbourhood increases, the prediction performance of the neighbours will decrease.

The method may include determining the number of data points the values of which are unlikely given the distributions associated with those data points.

This produces a measure of correlation.

The method may include determining the absolute difference between the actual value of each data point and a value predicted using the distribution associated with that data point.

Again, this provides a measure of local correlation.

The method may comprise iteratively performing the steps of (1) building a classification model based on a subset of data points selected from one or more representations, (2) assessing the performance of the model to determine whether its performance is within a desired range, and (3) adjusting the size of the subset until the performance of the model falls within the desired range.

It is known that the representations contain highly correlated data points and that some of the data points are not predictive of class. It is important that some models are not perfect, so that it may become apparent which areas of a separation pattern are important. Reducing the number of data points used in the classification procedure, by building models from random subsets of the original data, produces a range of classification performances. In the cases where the subset contains very few or no data points that are predictive of class, near chance performance is obtained. As more and more data points are included that are highly predictive, the discrimination results improve.

Thus, a method is provided of deriving the optimal number of data points to place within a subset in order to produce the expected range of performance values which allows models to be produced whose dimension is closer to that required to make the classification than to the original data dimensions.

For example, if there are 100 variables per class, it may be that a high performance model can be built using just 7 of these. Then, only a 7-dimensional model is needed, and not a 100-dimensional one. The other 93 variables may be very important for other reasons, but only 7 are needed for the classification at hand. This also produces improvements in the generality of fitted models.

The optimal number of data points depends on the goals of the analysis. In certain instances, slightly lower dimension is preferred to perfect performance. In other instances, perfect performance is preferred at the possible cost of slightly higher dimensionality.

By restricting the number of data points serving as input variables used to build a model, the model is more likely to fail. This is desirable if perfect performance is to be avoided.

In a preferred embodiment, during each iteration, steps (1) and (2) are repeated for subsets of uniform size but including different data points to obtain a distribution of model performances.

Step (2) may include determining whether a mean performance of the distribution is within the desired range.

Step (3) may include reducing the size of the subset if the mean performance is between a higher end of the desired range and perfect performance. Step (3) may include increasing the size of the subset if the mean performance is below a lower end of the desired range.

In the preferred embodiment, the desired range is from about 2.5 to about 3.0 standard deviations below perfect performance.

During the first iteration, step (1) may include arbitrarily selecting the size of the subset.

In step (1), the data points forming the subset may be selected randomly.

According to a third aspect of the invention, there is provided a method of analysing separation patterns, the method comprising building an importance map by iteratively recording performance values of classification models against locations in the importance map which correspond to locations in representations of separation patterns of data points used to build the classification models.

The method of the third aspect of the invention may include any feature of the method of the first or second aspect of the invention.

According to the first aspect of the invention, there is provided apparatus for performing operations on protein samples for the analysis of separation patterns, the apparatus comprising means for forming a representation of each separation pattern;
  means for building an importance map by iteratively recording performance values of classification models against locations in the importance map which correspond to locations in representations of separation patterns of data points used to build the classification models; and
  means for processing the importance map to identify important areas.

According to the second aspect of the invention, there is provided apparatus for performing operations on protein samples for the analysis of separation patterns, the apparatus comprising means for building an importance map by iteratively recording performance values of classification models against locations in the importance map which correspond to locations in representations of separation patterns of data points used to build the classification models; and means for processing the importance map to identify important areas.

According to the third aspect of the invention, there is provided apparatus for analysing separation patterns, the apparatus comprising means to build an importance map by iteratively recording performance values of classification models against locations in the importance map which correspond to locations in representations of separation patterns of data points used to build the classification models.

The representation includes a neighbourhood representing a region of the separation pattern, the neighbourhood including a plurality of data points. The apparatus of any aspect of the invention may include means for augmenting data by representing the entire region using each data point of the neighbourhood.

The apparatus of any aspect of the invention may include means for iteratively performing the steps of (1) building a classification model based on a subset of data points selected from one or more representations, (2) assessing the performance of the model to determine whether its performance is within a desired range, and (3) adjusting the size of the subset until the performance of the model falls within the desired range.

According to the invention, there is also provided an importance map comprising locations which correspond to locations of data points in representations of separation patterns, performance values of classification models being recordable at each location.

According to the invention, there is also provided storage means including the importance map of the invention.

According to the invention, there is also provided a computer program directly loadable into the internal memory of a digital computer, comprising software code portions for performing a method of the invention when said program is run on the digital computer.

According to the invention, there is also provided a computer program product directly loadable into the internal memory of a digital computer, comprising software code portions for performing a method of the invention when said product is run on the digital computer.

According to the invention, there is also provided a carrier, which may comprise electronic signals, for a computer program of the invention.

According to the invention, there is also provided electronic distribution of a computer program of or a computer program product or a carrier of the invention.

BRIEF DESCRIPTION OF THE DRAWINGS

In order that the invention may more readily be understood, a description is now given, by way of example only, reference being made to the accompanying drawings, in which:—

DETAILED DESCRIPTION OF THE INVENTION

Figure 2:
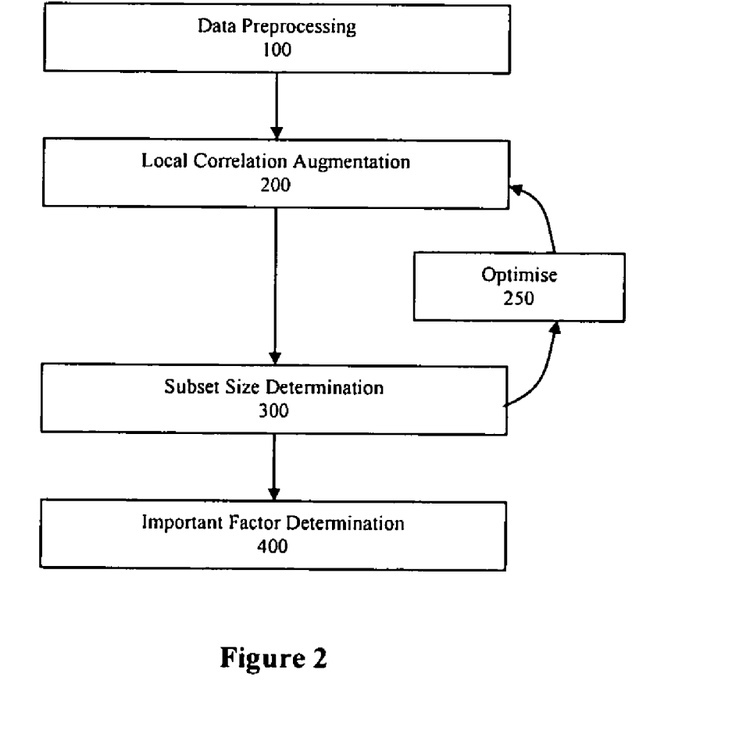
FIG. 2 is a flowchart representing a method of analysing separation patterns according to the invention.

FIG. 2 shows a method of analysing separation patterns according to the invention. The method includes the steps of data preprocessing 100; local correlation augmentation 200; subset size determination 300; optimisation 250 of steps 200 and 300; and important factor determination 400.

Data Preprocessing 100

In addition to the following steps, the step of data preprocessing 100 includes the standardisation of input data, and the separation of files to facilitate processing on multiple machines.

Combining Separation Data into Matrix Form

A number of samples each in one of several classes (for example control or treatment) is taken, a separation technique performed on those samples (for example 2D gel electrophoresis), and images made of the resulting separation patterns.

A multi-dimensional matrix of images stacked against their classifications is then produced.

In the case of a 2D separation technique, a 3D aligned dataset is produced including a number of images each representing a separation pattern in two of the dimensions, those dimensions being referred to as the sample plane, and including different experimental conditions (and replicates thereof) in the third dimension, the classification dimension.

Corrections

A correction for background offset is made.

Normalisation

In this embodiment, a nonlinear mapping that best overlays the cumulative grey level histogram between the images and a designated 'reference' image is performed. Alternatives include statistical standardisation where the mean of the image is set to zero and all grey.

Registration

Registration follows normalisation as the registration performance is better on normalised images. In a variant, registration is followed by a second normalisation step.

A pixel-level transformation is produced that maps corresponding data points to one another in a multi-dimensional matrix of images representing separation patterns. The transformation can be manual, semi-automatic or fully automatic.

Registering the images to a high degree of accuracy means that each pixel can be considered as a measurement. Differences between pixels across images are thus related to experimental conditions.

Preferably, corrections are made for inter gel differences (for example normalisation and offset correction), allowing statistical measures to be applied to each pixel individually.

In this embodiment, the registration is performed using a mutual information-based error metric via stepped gradient descent. In another embodiment, the registration is performed using a manually assisted image metric based warp.

Data Reduction

The multidimensional matrix is then processed using a data reduction mechanism to reduce the dimensionality of the data.

In this embodiment, a principal component analysis (PCA) technique is used to select a reduced number of dimensions for further use. In other embodiments, partial least squares (PLS) or independent component analysis (ICA) techniques are used.

Local Correlation Augmentation 200

Figure 3A:
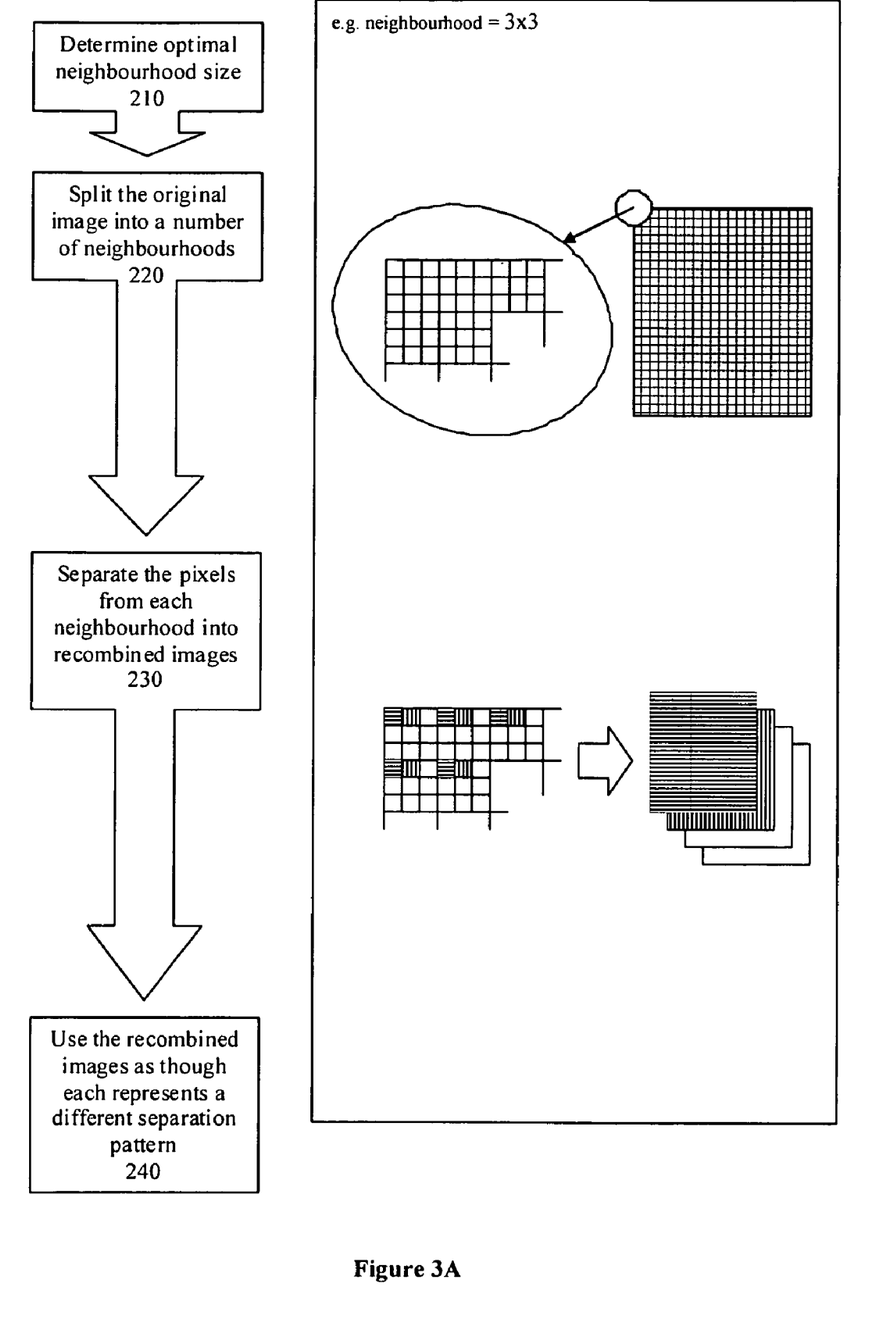
FIG. 3A is a flowchart representing a method of data augmentation according to the invention.

FIG. 3A is a flowchart representing a method of augmenting data according to the invention, the method being applied in relation to a single image. The process is repeated for a number of images representing different separation patterns.

In step 210, the optimal size of a neighbourhood is determined. In this embodiment, the size of each neighbourhood is 3×3 pixels.

The neighbourhood may be of such a size that it covers uncorrelated features. To determine whether or not this is the case, a distribution of performance values of classification models can be built using a 3×3 neighbourhood, for example, and compared to a distribution produced using a 5×5 neighbourhood. Criteria can be selected based on the neighbourhood sizes if a statistical change in the distributions is detected. For example, F-ratio or student t tests provide good tests where a probability threshold can be chosen which allows a threshold based on the probability that the distributions significantly differ in means. Similarly, non-parametric tests could be used.

Alternatively, pixel based statistical prediction models can be built from the whole image to see how well the value of a given pixel can be predicted, given a set of neighbourhoods. If the prediction deteriorates then the correlation is dropping. This technique is related to a Bayesian approach. For example, for each pixel of a given value, the neighbouring pixels can be added to a distribution for that given value. This results in a distribution of likely neighbourhood values for each pixel in the image. The distributions of the neighbours of each pixel value can be used to predict how likely the value is, given what the case is in the rest of the image. If all of the neighbours indicate that the pixel value is unlikely, that pixel is probably a noise feature. This approach only works if the neighbours are good predictors of each other. As the size of the neighbourhood increases, the prediction performance of the neighbours will decrease.

Based on the above approach, a determination of whether the size of the neighbourhood is too large can be made in one or both of two ways. Firstly, the number of pixels which are classed as unlikely given their neighbours can be determined. This produces a measure of correlation. Secondly, the neighbours can be used to predict the most likely values of pixels, followed by recording the absolute differences between predicted and actual values. Again, this provides a measure of local correlation.

In step 220, the original image is separated into a number of neighbourhoods.

Figure 3B:
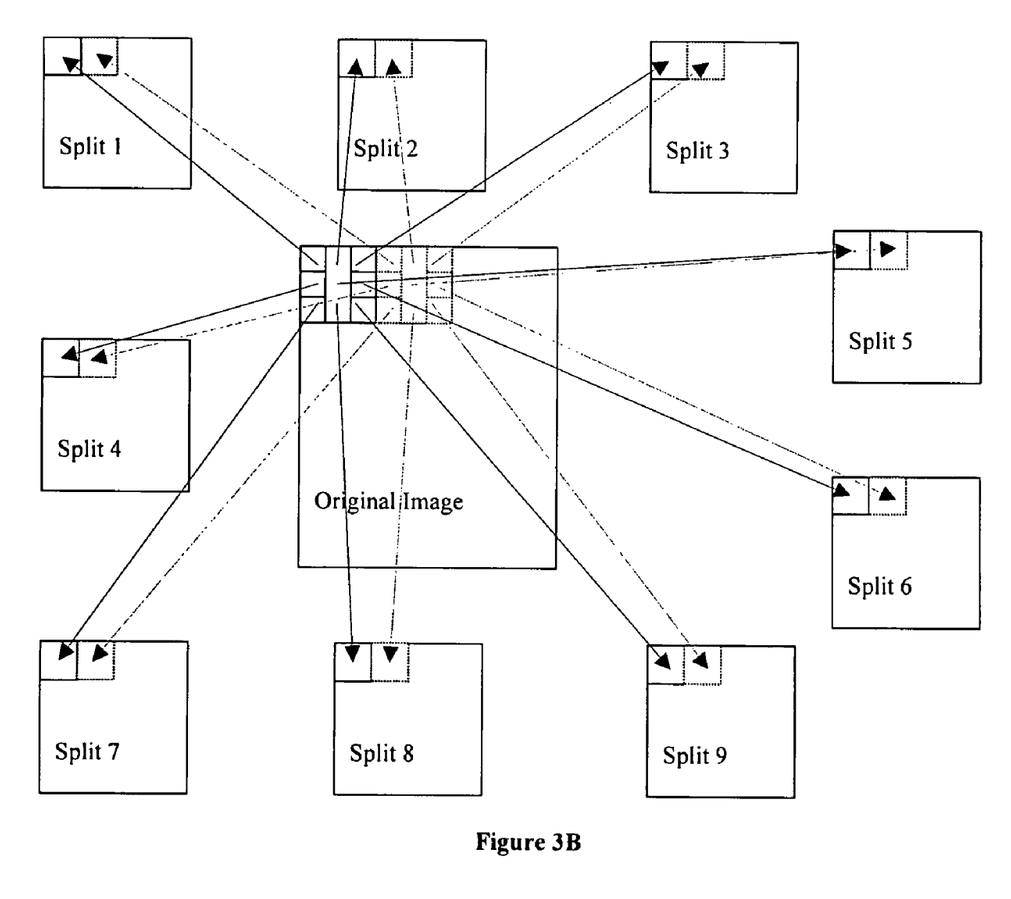
FIG. 3B illustrates successive steps of the method of FIG. 3A being performed on an image.

FIG. 3B illustrates step 230, in which the pixels from each neighbourhood in the original image are separated into recombined images.

The number of recombined images is equal to the number of locations in the neighbourhood. For ease of reference, the locations of the pixels in each neighbourhood will be referred to as locations 1 to 9, reading from left to right and top to bottom. As seen, a neighbourhood of size 3×3 pixels, having nine locations, gives rise to nine recombined images, designated "Split 1" to "Split 9".

Each recombined image is associated with a particular location of a pixel in a neighbourhood. For example, a pixel at location 1 in a neighbourhood is separated into recombined image "Split 1", a pixel at location 2 is separated into "Split 2", and so on.

The separation of pixels into recombined images is performed for each neighbourhood.

The location of a data point in a recombined image corresponds to the location of its neighbourhood in the original image.

For example, the neighbourhood shown in solid lines in FIG. 3B is in the top left-hand corner of the original image. Therefore, the pixel at location 3 of that neighbourhood is separated into the top left-hand corner of recombined image "Split 3". The pixel at location 3 of the neighbourhood immediately to the right of the top left-hand neighbourhood, shown in dotted lines, will be separated into a location in Split 3 which is immediately to the right of the pixel separated from the neighbourhood shown in solid lines, and so on.

For a neighbourhood of size 3×3 pixels, each recombined image is one third of the width and height of the original image.

Referring again to FIG. 3A, in step 240, the recombined images are used as new class examples. The effect of this is that each pixel in a recombined image is taken as being representative of the region of the separation pattern covered by the neighbourhood from which that pixel was taken.

It should be understood that it is not necessary physically to separate pixels into recombined images and to store the recombined images. For example, in a variant, the augmentation is performed during the preparation for each iteration of an importance map building step (described below), by taking pixels directly from unaugmented images.

Subset Size Determination 300

Figure 4:
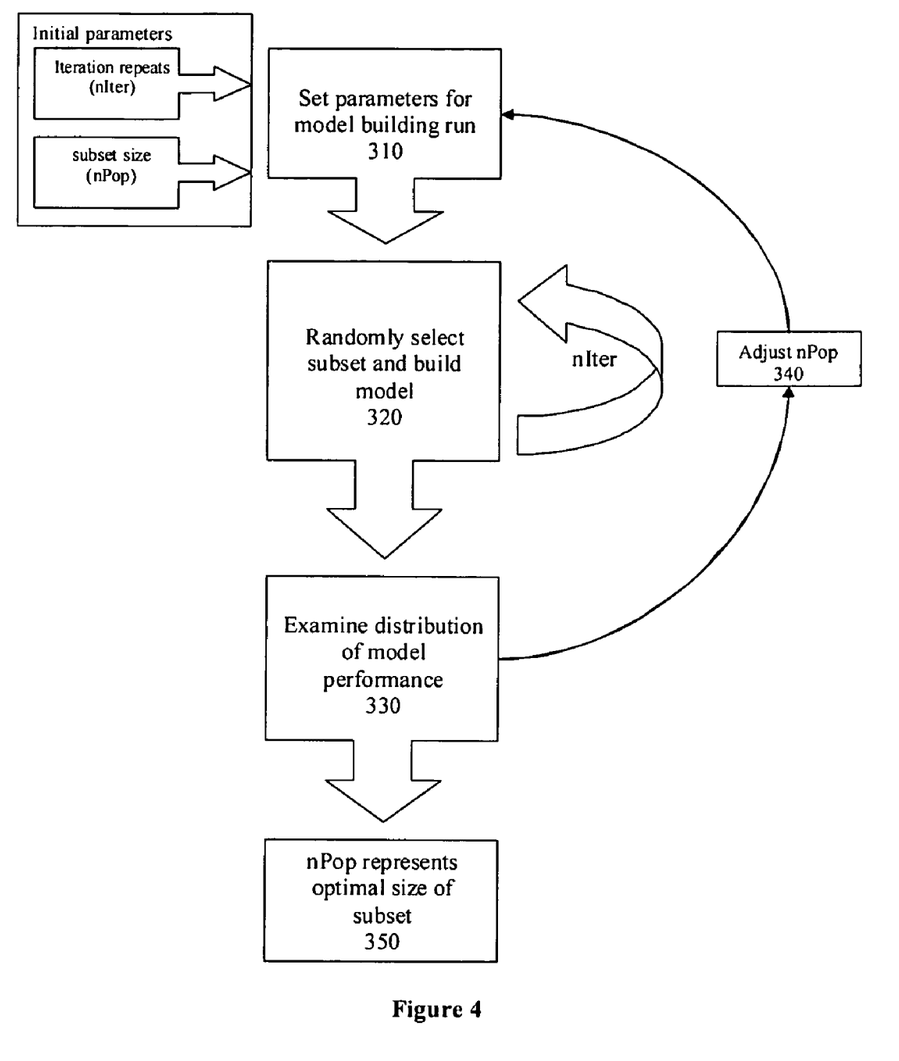
FIG. 4 is a flowchart representing a method of sample size determination according to the invention.

FIG. 4 is a flowchart representing a method of subset size determination according to the invention.

In step 310, initial values for the number of data points in a subset, nPop, and the number of iterations, nIter, for the model-building step (step 320) are arbitrarily selected.

Typically, the initial values effect how long the process takes to optimise, more than whether the optimisation works or not.

In step 320, a number nPop of data points from one or more representations are randomly selected to form a subset. The subset is partitioned into a training set and a test set, and a classification model is built based on the training set. This step is repeated nIter times, each time using a subset including nPop randomly-selected data points.

In step 330, the performance of each model is assessed, using the test set associated with each model, and a distribution of model performances is produced. A mean performance value and the standard deviation of the distribution are then calculated, before it is determined whether the mean performance falls within a desired range, which in this embodiment is from about 2.5 to about 3.0 standard deviations below perfect performance.

If the mean performance falls outside of the desired range, the process proceeds to step 340, and then back to step 310. In step 340, if the mean performance is less than about 2.5 standard deviations below perfect performance, nPop is reduced. If the mean performance is more than about 3.0 standard deviations below perfect performance, nPop is increased.

If the mean performance falls within the desired range, the current value of nPop is taken as the optimal subset size, in step 350.

Optimisation 250

To determine the important factors we need to be able to build models where it is possible to get less than perfect performance (or else we would not be able to tell which pixels were important). To drop the level of performance, we can drop the amount of information the modeling procedure receives. There are several factors that control model performance, but the two which are easiest to control are the size of the neighbourhood used in step 200 and the size of the subset used in step 300.

One option is to select a particular neighbourhood size and adjust the subset size to get the desired range of model performances. If the performance cannot be sufficiently reduced using subset size alone, the neighbourhood size can be reduced and the procedure repeated.

In some circumstances, for example when using MS data, step 200 is not required, and so the above procedure is not appropriate.

Important Factor Determination 400

Figure 5:
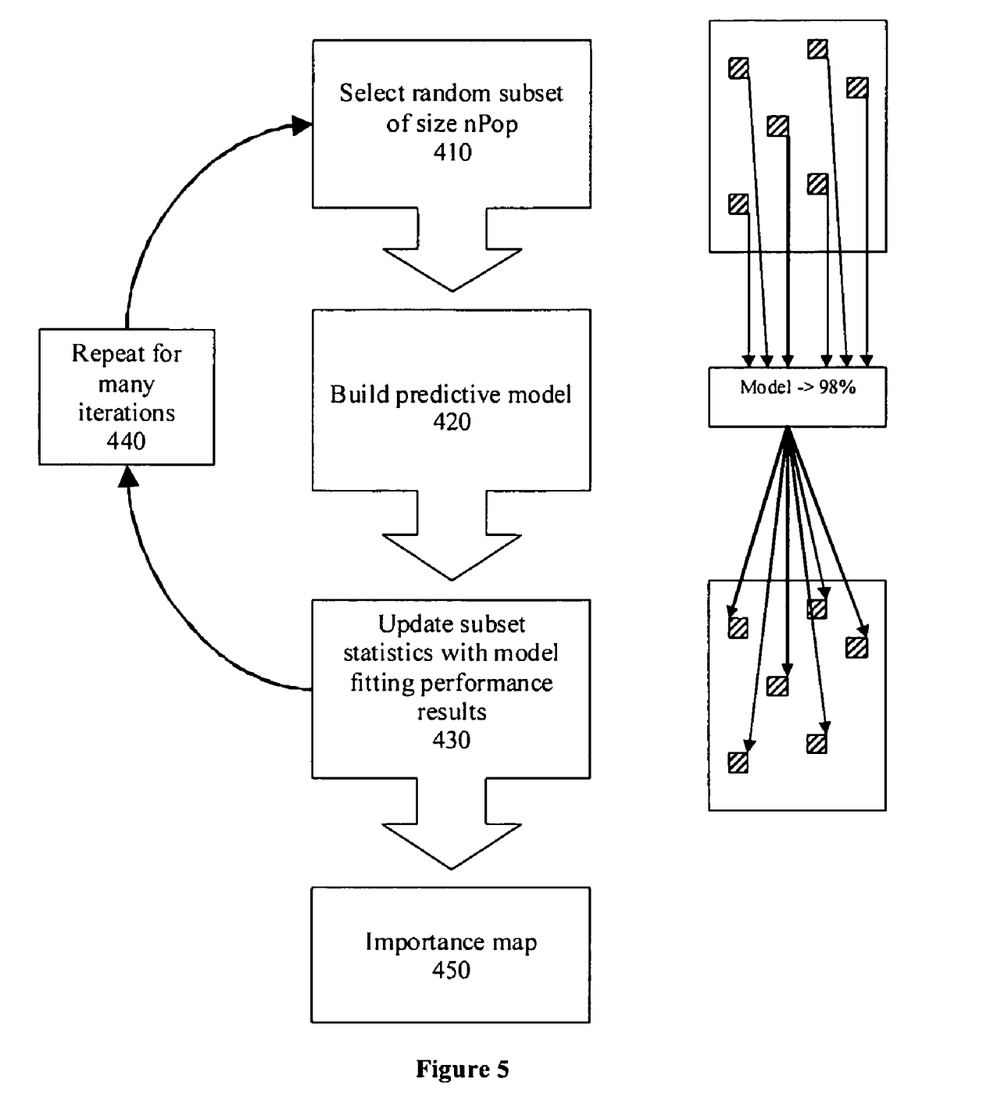
FIG. 5 is a flowchart representing a method of important factor determination according to the invention.

FIG. 5 illustrates the method of important factor determination in more detail.

In step 410, a subset of size nPop is built. This step includes randomly selecting particular locations in a reference image, and building the subset by combining pixels taken from each image at the selected locations. In a variant, a list of pixels within an image is made and randomly shuffled.

The subset is then randomly partitioned into a training set and a test set.

In step 420, a statistical learning technique is used on the training set to build a classification model.

In this embodiment, flexible discriminant analysis is used. Other embodiments use discriminant analysis, artificial neural networks, regression trees, genetic algorithms, support vector machines, or any classifier technology.

In step 430, the performance of the model is assessed using the test set to obtain a performance value. Such assessment involves using the model to predict the class of each pixel in the test set, and recording the resulting performance value in the importance map.

As the images are registered, each image has the same number and arrangement of pixels. For example, if the reference image is 1000×1000, each other image will be 1000×1000.

The importance map has a corresponding number and arrangement of pixels. The performance value is recorded in the importance map at locations which correspond to the locations of the pixels used to build the classification model.

The performance value can be recorded as a percentage performance, and/or a distribution of performance values. In this embodiment, the distribution is in the form of a confusion matrix. An example confusion matrix is shown below.

|  | Normal (predict) | Cancer (predict) |
|---|---|---|
| normal | 47 | 3 |
| cancer | 2 | 48 |

In this case, the model correctly predicted the class of 47 samples in the normal class and of 48 samples in the cancer class. A performance value in the form of a percentage can be obtained from these values (47+48=95%).

The model incorrectly predicted that 3 samples in the normal class were in the cancer class. More significantly, the model predicted that 2 of the samples in the cancer class were in the normal class.

It may be that predicting a sample in the normal class as being in the cancer class is preferable to predicting a sample in the cancer class as being in the normal class.

In that case, the following model may be more preferable even though its percentage prediction performance is lower.

|  | Normal (predict) | Cancer (predict) |
|---|---|---|
| normal | 37 | 13 |
| cancer | 0 | 50 |

Accordingly, having access to the whole confusion matrix is important.

Steps 410 to 430 are repeated for many iterations. In this embodiment, steps 410 to 430 are iteratively performed until the performance value at every location converges to within a predetermined tolerance. (step 440). Alternatively, a fixed number of iterations could be performed.

The result of the above process is that an importance map is obtained (step 450), which, for each location, indicates the performance of models which included pixels at that location.

Software

Figure 6:
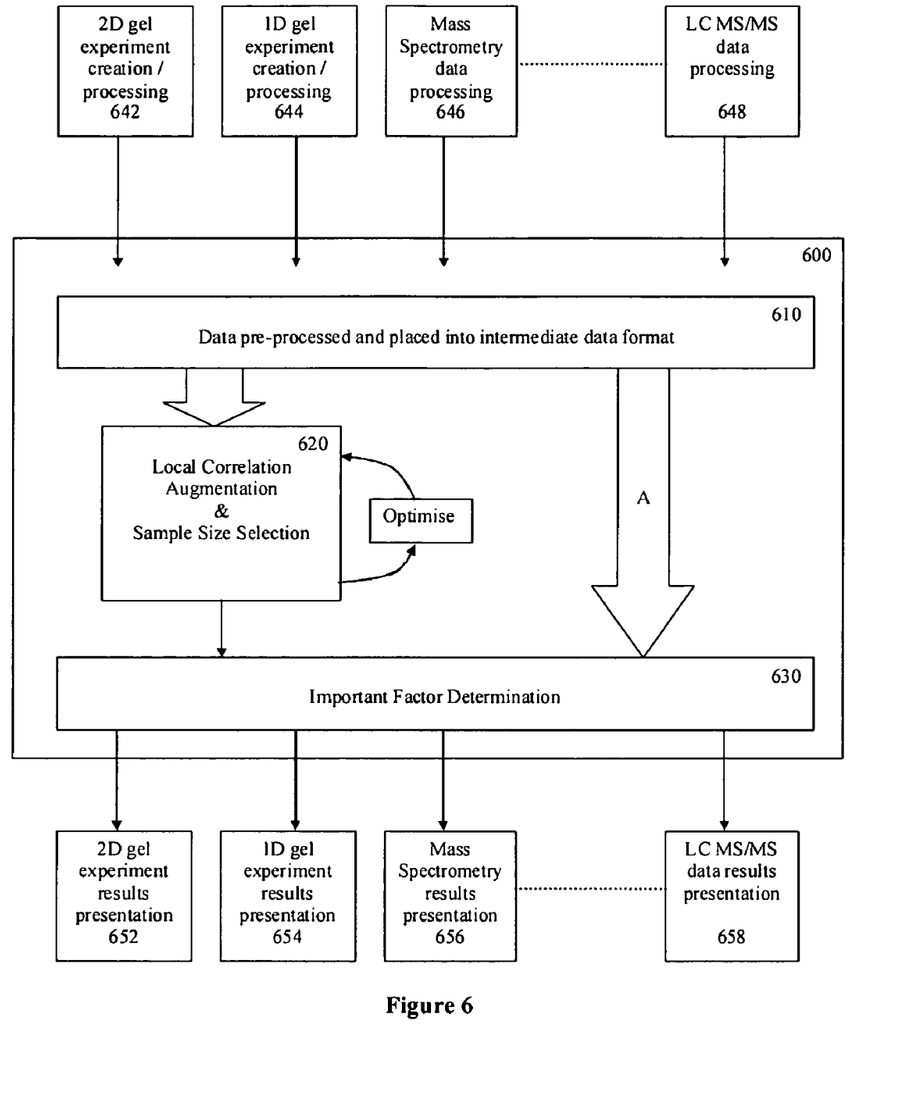
FIG. 6 is a schematic diagram of software according to the invention.

FIG. 6 is a schematic diagram of a software entity 600 according to the invention.

The software entity 600 is a generic automated analysis block that operates on supervised data across modalities, i.e. it is not specific to 2D gels, 1D gels, or mass spectra, for example.

In a preferred embodiment, the software entity is incorporated into multi-application computer software for running on standard PC hardware under Microsoft® Windows®. However, it is to be understood that the invention is platform independent and is not limited to any particular form of computer hardware.

The software entity 600 includes a data preprocessing block 610, for performing step 100 of the method; a local correlation augmentation and subset size determination block 620, for performing steps 200, 250 and 300 of the method; and an important factor determination block 630, for performing step 400.

The software entity 600 receives input data from one of a number of input blocks 640, each input block 640 representing a different separation technique. FIG. 6 shows exemplary input blocks designated 642, 644, 646 and 648.

The input data is in the form of several vectors, each having a class label. Each vector includes a number of 16-bit integer or double precision floating point numbers. The input blocks 640 create a uniform format from the diverse formats of data obtained using the various separation techniques. In addition, there is a secondary metadata file that includes a description of the original data format.

In this embodiment, only one input block is used at a time. In a variant, more than one input block is used simultaneously.

Metadata, including class information, is passed directly from the data preprocessing block 610 to the important factor determination block 630, as indicated by arrow A.

The software entity 600 sends output data to a number of output blocks 650. FIG. 6 shows exemplary output blocks designated 652, 654, 656 and 658. Each output block 650 corresponds to an input block 640.

The output blocks 650 receive results in a generic form and map the results to a more accessible form, for example an image or trace. In block 652, the importance map is mapped back onto one of the images from the set. In block 654, the importance map is mapped back to a gel image; in block 656 to a trace (656); and in block 658 to a 2D representation of the LC MS data.

When the software entity 600 is commercially exploited, the input blocks 640 and output blocks 650 are tailored to the user's specific requirements, which distinction is transparent to the user.

EXAMPLES OF THE INVENTION

Figure 7:
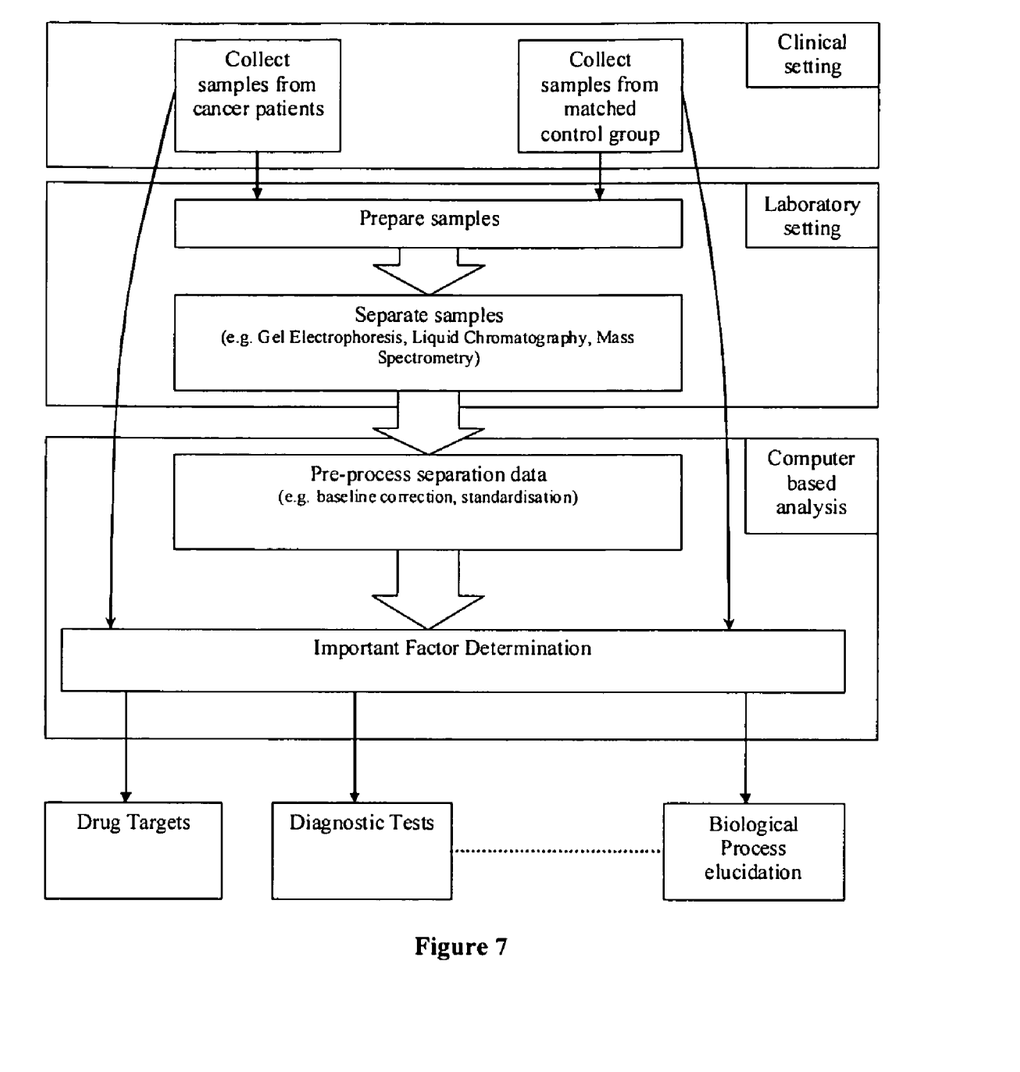
FIG. 7 is a flowchart representing an exemplary procedure according to the invention.

FIG. 7 is a flowchart representing an exemplary procedure according to the invention.

The procedure is undertaken in three different settings: a clinical setting, a laboratory setting, and a computer-based setting.

In the clinical setting, samples are collected from both cancer patients and matched control group patients, the samples being classified accordingly.

In the laboratory setting, the samples are prepared and separated using one or more separation techniques.

It is to be understood that the operations performed in the clinical and laboratory settings are known to those skilled in the art.

In the computer-based setting, a software entity 600 according to the invention performs the methods described above to obtain a number of importance maps.

It may be assumed that the important areas found by the analysis (be they spots in 2D gels or mass values in mass spectra) are caused by underlying differences between the class groups.

In the case of non-cancer versus cancer it may be assumed that the changes in protein expression (manifested by changes in the spots or mass spectra) are due to the disease. Once these candidates are found, the next step is to attempt an identification. This is usually done by comparison with public databases, with a view to finding a match (although if this does not happen there are other avenues).

The identification may provide other useful research information, such as with which biological processes the protein is usually involved.

In addition, structural information can be ascertained and binding sites of known compounds found. If compounds that interact with the identified protein can be found, it may be possible to alter the disease process.

With reference to FIG. 7, the importance maps are used in several different ways, including drug targets, diagnostic tests and biological process elucidation. It should be understood that these are examples only, and not an exhaustive list.

Drug Targets
  This process involves the following steps:—
  Identification of the proteins suggested by the process;
  Use of further research to attempt to find the disease process;
  Obtaining of structural information for the proteins involved;
  Ascertaining of potential binding sites on the proteins and comparison to a database of synthetic compounds;
  Discovery of something that disrupts the disease process with the minimum disruption to other systems (side effects).

Diagnostic Tests
  This process involves the following steps:—
  Ascertaining of some subset or combination of identified areas that allow the different disease states to be predicted;
  Verification of this on a larger population;
  Potentially providing a test, if successful up to this point, but more usually:
  Development of antibody tests that bind to the identified proteins, permitting a much simpler test.

Biological Process Elucidation
  This process involves the following steps:—
  Identification of the proteins that appear to be involved in the process;
  Examination of research to see if this protein has been well categorized, and if not, look for homologues;
  Building of a hypothesis for how the systems may be working in normal and disease states;
  Design of further experiments to test the hypothesis.

It is to be understood that, while examples of the invention have been described involving software, the invention is equally suitable for being implemented in hardware, or any combination of hardware and software.

Some portions of the preceding description are presented in terms of algorithms and symbolic representations of operations on data bits within a machine, such as computer memory. These algorithmic descriptions and representations are the ways used by those skilled in the data processing arts to most effectively convey the substance of their work to others skilled in the art. An algorithm includes a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussions, terms such as "processing" or "computing" or "calculating" or "determining" or "displaying" or the like, refer to the action and processes of a computer system, or similar computing device, that manipulates and transforms data represented as physical (e.g., electronic) quantities within the computer system's registers and memories into other data similarly represented as physical quantities within the computer system memories or registers or other such information storage, transmission or display devices.

There is also provided electronic distribution of a computer program of or a computer program product or a carrier of the invention. Electronic distribution includes transmission of the instructions through any electronic means such as global computer networks, such as the world wide web, Internet, etc. Other electronic transmission means includes local area networks, wide area networks. The electronic distribution may further include optical transmission and/or storage. Electronic distribution may further include wireless transmission. It will be recognized that these transmission means are not exhaustive and other devices may be used to transmit the data and instructions described herein.

The invention claimed is:

1. A method of performing operations on protein samples for the analysis of separation patterns, the method comprising:
   separating a plurality of protein samples to produce a plurality of respective separation patterns;
   forming a representation of each separation pattern;
   building, using a computer, an importance map by iteratively recording performance values of classification models against locations in the importance map which correspond to locations in representations of separation patterns of data points used to build the classification models; and
   computer processing the importance map to identify important areas.

2. A computerized method of performing operations on protein samples for the analysis of separation patterns, the method comprising building, in a computing device, an importance map by iteratively recording performance values of classification models against locations in the importance map which correspond to locations in representations of separation patterns of data points used to build the classification models; and processing, in a computing device, the importance map to identify important areas.

3. The method of claim 1 including the step of building a classification model based on a subset of the data points in the representations.

4. The method of claim 1 including iteratively performing:
   (1) electronically building a subset including data points taken from a number of representations and stored in memory;
   (2) partitioning, in a computer, the subset into a training set and a test set;
   (3) building, using a computer, a classification model based on the training set;
   (4) assessing, using a computer, the performance of the classification model on the test set to obtain a performance value; and
   recording, in memory, the performance value against locations in the importance map which correspond to the locations in the representations of the data points used to build the model.

5. The method of claim 1 including iteratively performing the method until the performance value at every location converges to within a predetermined tolerance.

6. The method of claim 4 wherein building a subset includes
   (1a) selecting particular locations in a reference representation; and
   (1b) electronically building the subset by combining data points taken from each representation at the selected locations.

7. The method of claim 6 wherein selecting particular locations in a reference representation includes randomly selecting the locations.

8. The method of claim 6 wherein selecting particular locations in a reference representation includes making and randomly shuffling a list of data points within a representation.

9. The method of claim 1 wherein building the classification model is using any one or more of the following techniques: discriminant analysis; flexible discriminant analysis; artificial neural networks; regression trees; genetic algorithms; or support vector machines.

10. The method of claim 4 including normalizing the representations prior to building the subset of data points.

11. The method of claim 10 including registering the representations of separation patterns after normalizing.

12. The method of claim 11 including performing data reduction, to reduce the dimensionality of the data region after registering the representations of separation patterns.

13. The method of claim 12 wherein performing data reduction includes any one or more of the following techniques: partial least squares; independent component analysis; or principal component analysis.

14. The method of claim 1 including recording an average performance value.

15. The method of claim 1 including recording a distribution of performance values.

16. The method of claim 15 wherein the distribution comprises a confusion matrix.

17. The method of claim 1 wherein the representation includes a neighborhood representing a region of the separation pattern, the neighborhood including a plurality of data points, the method including augmenting data by representing the entire region using each data point of the neighborhood.

18. The method of claim 17 wherein the data augmentation step includes separating the data points of the neighborhood into respective recombined representations, the location of a data point in a recombined representation corresponding to the location of its neighborhood in the representation.

19. The method of claim 18 comprising associating each recombined representation with a particular location of a data point in a neighborhood.

20. The method of claim 19 including varying the association of recombined representations with locations between neighborhoods.

21. The method of claim 17 including varying the position of a particular neighborhood in relation to the representation.

22. The method of claim 1 including comparing a first distribution built using neighborhoods of a first size to a second distribution built using neighborhoods of a second size and selecting criteria based on the first and second sizes if a statistical change in the distributions is detected.

23. The method of claim 22 wherein F-ratio or student t tests are used to determine a probability threshold based on the probability that the distributions significantly differ in means.

24. The method of claim 22 wherein non-parametric tests are used.

25. The method of claim 1 including building a distribution in respect of each data point, the distribution including values of neighboring data points.

26. The method of claim 25 including determining the number of data points the values of which are unlikely given the distributions associated with those data points.

27. The method of claim 25 including determining the absolute difference between the actual value of each data point and a value predicted using the distribution associated with that data point.

28. A computerized method comprising:
(1) building, in a computing device, a classification model based on the subset of data points selected from one or more representations of protein samples, and
building, using a computer, an importance map by iteratively recording performance values of classification models against locations in the importance map which correspond to locations in representations of separation patterns of data points used to build the classification models.

29. The computerized method of claim 28 wherein, during each iteration, building a classification model and assessing are repeated for subsets of uniform size but including different data points to obtain a distribution of model performances.

30. The computerized method of claim 29 wherein building the importance map includes determining whether a mean performance of the distribution is within the desired range.

31. The computerized method of claim 30 wherein building the importance map includes reducing the size of the subset if the mean performance is between a higher end of the desired range and perfect performance.

32. The computerized method of claim 30 wherein building the importance map includes increasing the size of the subset if the mean performance is below a lower end of the desired range.

33. The computerized method of claim 28 wherein the desired range is from about 2.5 to about 3.0 standard deviations below perfect performance.

34. The computerized method of claim 28 wherein, during the first iteration, building a classification model includes arbitrarily selecting the size of the subset.

35. The computerized method of claim 28 wherein, in building a classification model, the data points forming the subset are selected randomly.

36. Apparatus for performing operations on protein samples for the analysis of separation patterns, the apparatus comprising
means for forming a representation of each separation pattern;
means for building an importance map by iteratively recording performance values of classification models against locations in the importance map which correspond to locations in representations of separation patterns of data points used to build the classification models; and
means for processing the importance map to identify important areas.

37. Apparatus for performing operations on protein samples for the analysis of separation patterns, the apparatus comprising means for building an importance map by iteratively recording performance values of classification models against locations in the importance map which correspond to locations in representations of separation patterns of data points used to build the classification models; and means for processing the importance map to identify important areas.

38. Apparatus for analyzing separation patterns, the apparatus comprising: computerized means for building an importance map by iteratively recording performance values of classification models against locations in the importance map which correspond to locations in representations of separation patterns of data points used to build the classification models; and a memory for storing the importance map.

39. The apparatus of claim 36 wherein the representation includes a neighborhood representing a region of the separation pattern, the neighborhood including a plurality of data points, the apparatus including means for augmenting data by representing the entire region using each data point of the neighborhood.

40. The apparatus of claim 36 including means for iteratively performing the steps of (1) building a classification model based on a subset of data points selected from one or more representations, (2) assessing the performance of the model to determine whether its performance is within a desired range, and (3) adjusting the size of the subset until the performance of the model falls within the desired range.

41. A non-transitory computer-readable medium including computer executable instructions for performing a method, the instructions comprising: the method comprising:
forming a representation of each of a plurality of separation patterns;
building an importance map by iteratively recording performance values of classification models against locations in the importance map which correspond to locations in representations of separation patterns of data points used to build the classification models; and
processing the importance map to identify important areas.

42. The computer-readable medium of claim 41, further comprising separating a plurality of protein samples to produce a plurality of respective separation patterns.

43. The method of claim 11, wherein registering the representations of separation patterns is before building the subset.

44. The method of claim 12, wherein performing data reduction is before building the subset.

45. The method of claim 44, wherein performing data reduction includes any one or more of the following techniques: partial least squares; independent component analysis; or principal component analysis.

46. The method of claim 1, wherein forming a representation of each separation pattern includes normalizing the representations.

* * * * *

UNITED STATES PATENT AND TRADEMARK OFFICE
CERTIFICATE OF CORRECTION

PATENT NO. : 7,747,048 B2
APPLICATION NO. : 11/212477
DATED : June 29, 2010
INVENTOR(S) : Ian Morns et al.

It is certified that error appears in the above-identified patent and that said Letters Patent is hereby corrected as shown below:

Column 15

Line 40 (Claim 4, line 2) delete "(1)"

Line 43 (Claim 4, line 5) delete "(2)"

Line 45 (Claim 4, line 7) delete "(3)"

Line 47 (Claim 4, line 9) delete "(4)"

Line 59 (Claim 6, line 3) delete "(1a)"

Line 61 (Claim 6, line 5) delete "(1b)"

Column 16

Line 6 (Claim 9, line 2) delete "is" between "model" and "using"

Column 17

Line 2 (Claim 28, line 2) delete "(1)"

Column 18

Line 28 (Claim 41, line 3) delete "the method comprising:" after "the instructions comprising:"

Signed and Sealed this
First Day of March, 2011

David J. Kappos
*Director of the United States Patent and Trademark Office*